United States Patent [19]

Takahashi et al.

[11] Patent Number: 4,661,234

[45] Date of Patent: Apr. 28, 1987

[54] AIR-FUEL RATIO SENSOR AND APPARATUS USING THE SAME

[75] Inventors: Hideaki Takahashi; Haruyoshi Kondo; Takashi Takeuchi; Kiyoharu Hayakawa, all of Aichi, Japan

[73] Assignee: Kabushiki Kaisha Toyota Chuo Kenkyusho, Aichi, Japan

[21] Appl. No.: 812,907

[22] Filed: Dec. 23, 1985

[30] Foreign Application Priority Data

Dec. 28, 1984 [JP] Japan .............................. 59-274586

[51] Int. Cl.$^4$ ........................................... G01N 27/58
[52] U.S. Cl. .................................... 204/406; 204/412; 204/425; 204/426; 338/34
[58] Field of Search ............... 204/425, 406, 412, 426, 204/15; 338/34; 60/276; 123/489

[56] References Cited

U.S. PATENT DOCUMENTS

| | | | |
|---|---|---|---|
| 4,264,425 | 4/1981 | Kimura et al. | 60/276 X |
| 4,302,312 | 11/1981 | Ishitani et al. | 204/426 X |
| 4,472,262 | 9/1984 | Kondo et al. | 204/408 |
| 4,500,412 | 2/1985 | Takahashi et al. | 204/425 |
| 4,510,036 | 4/1985 | Takeuchi et al. | 204/425 |
| 4,574,264 | 3/1986 | Takahashi et al. | 338/34 |
| 4,578,172 | 3/1986 | Yamada et al. | 204/412 |

Primary Examiner—G. L. Kaplan

[57] ABSTRACT

An air-fuel ratio sensor comprising a limiting electric current type oxygen sensor portion, having a sequential stacking on a porous substrate of a first electrode with high gas permeability, a solid electrolytic thin film having a specific crystal orientation, a thickness of 0.1 to 30 μm, and good crystallinity. The limiting electric current type oxygen sensor portion and second electrode with a high gas permeability, is arranged and connected in parallel with a resistive type oxygen sensor portion having interdigital electrodes formed on one or both major surfaces of an oxide semiconductor thin film, the resistance of which changes in accordance with oxygen partial pressure. The air-fuel ratio sensor also has a sensor heater formed on one surface of the porous substrate around the sensor portions. The overall structure of the sensor is coated with a porous ceramic coating to which a catalyst is added.

7 Claims, 24 Drawing Figures

AIR-FUEL RATIO SENSOR AND APPARATUS USING THE SAME

BACKGROUND OF THE INVENTION

I. Field of the Invention

The present invention relates to an air-fuel ratio sensor and an air-fuel ratio detecting apparatus using the same.

II. Description of the Prior Art

Various conventional air-fuel ratio sensors have been proposed. In a conventional air-fuel ratio sensor (Japanese Laid-Open Patent Application No. 58-61455), a sensor for detecting oxygen gas in an exhaust gas from a vehicle or the like, a resistive type oxide semiconductor sensor whose resistance changes abruptly at a theoretical air-fuel ratio (to be referred to as $\lambda=1$ hereinafter), and a limiting electric current type oxygen sensor whose current changes in accordance with ambient oxygen concentration upon application of a constant voltage thereto are electrically connected in parallel with each other, and the resulting sensor is heated by a heater arranged near the sensor. In another conventional air-fuel ratio sensor (Japanese Laid-Open Patent Application No. 58-30654), the above three component sensors are formed adjacent to each other on a substrate with a heater.

Although these air-fuel ratio sensors have a compact structure and high response with an air-fuel ratio detection range unmatched by other conventional sensors, there is still room for improvement. In general, exhaust gas temperatures in the engine of a vehicle or the like vary with different operation states, so a wide operating temperature range from a low temperature to a high temperature is required for an air-fuel ratio sensor. In addition to accurate detection of the air-fuel ratio, low power consumption is also necessary.

No conventional air-fuel sensors, however, can meet these requirements.

In order to obtain a wide measurement range by combining two types of sensors, their respective processing circuits must be integrated to obtain a single air-fuel ratio output, since two independent processing circuits limit the compactness of the system configuration. According to extensive studies by the present inventors, such integration entailed a problem to be solved.

A large current flows in the limiting electric current type oxygen sensor portion in regions where the air-fuel ratio $\lambda$ is smaller than 1, irrespective of the value of $\lambda$, thus establishing a two-valued function.

In order to solve the above problem, the limiting electric current type oxygen sensor portion is set to switch off when the air-fuel ratio $\lambda$ is less than 1. However, simple switching causes pulse noise, thus presenting yet another problem.

SUMMARY OF THE INVENTION

It is an object of the present invention to provide an air-fuel ratio sensor and an apparatus using the same, wherein the conventional problems described above are solved and a wide measurement range between a theoretical air-fuel ratio (to be referred to as $\lambda=1$ hereinafter) and an excess air region (to be referred to as a lead region) can be obtained.

In order to achieve the above object of the present invention, a resistive type oxygen sensor (i.e., an oxide semiconductor sensor), a limiting electric current type oxygen sensor, and a heater are formed in combination on a porous alumina substrate, and proper characteristics of these components are selected.

According to an air-fuel ratio sensor of the present invention, a limiting electric current type oxygen sensor portion, obtained by sequentially stacking on a porous substrate (having a porosity of 2% to 40% and a pore diameter of 0.02 μm to 1.2 μm) a first electrode with a high gas permeability, a solid electrolytic thin film having a specific crystal orientation, a thickness of 0.1 to 30 μm, and good crystallinity, and a second electrode with a high gas permeability, is arranged and connected in parallel with a resistive type oxygen sensor portion having interdigital electrodes formed on one or both major surfaces of an oxide semiconductor thin film, the resistance of which is largely changed by oxygen partial pressure. The air-fuel ratio sensor also has a sensor heater formed on at least one surface of the porous substrate. The overall structure of the sensor is preferably coated with a porous ceramic coating to which a catalyst is added.

An air-fuel ratio detecting apparatus as a combination of an air-fuel ratio sensor and a sensor output processing circuit according to the present invention is characterized by comprising a limiting electric current measuring voltage source for generating a voltage to be applied to a limiting electric current type oxygen sensor portion, an electric current detector for detecting an electric current flowing through the limiting electric current type oxygen sensor portion upon application of the voltage thereto, a resistance detector for detecting the resistance of a resistive type oxygen sensor portion, a comparator/discriminator for a comparing an output from the resistance detector with a reference value and discriminating whether an air-fuel ratio represents a fuel rich or fuel lean state, a controller for controlling switching connection between the limiting electric current measuring voltage source and the limiting electric current type oxygen sensor portion such that the limiting electric current measuring voltage source is connected to the limiting electric current type oxygen sensor portion when a predetermined period of time has elapsed after the fuel rich state changes to the fuel lean state, and that the limiting electric current measuring voltage source is disconnected from the limiting electric current type oxygen sensor portion when the fuel lean state changes to the fuel rich state, and an output signal adding section for adding an output signal from the limiting electric current type oxygen sensor portion and an output signal from the resistive type oxygen sensor portion and generating a signal representing an air-fuel ratio.

By using a porous alumina substrate having a resistive type oxygen sensor, which is formed on the porous alumina substrate to detect an air-fuel ratio in a wide range between $\lambda=1$ and the lean air-fuel region and the resistance of which changes abruptly at $\lambda=1$, and a limiting electric current type oxygen sensor, which is formed adjacent to the resistive type oxygen sensor and the output current of which increases linearly in proportion to the oxygen concentration, the resistive type oxygen sensor can be oxidized or reduced from both the porous catalyst-carrying coating layer and the catalyst-carrying porous alumina substrate, thereby obtaining high response. Furthermore, deposits such as soot or tar can be combusted on the coating layer and the alumina substrate, so that the coating layer and the alumina do not clog. In the limiting electric current type oxygen sensor, the porous alumina substrate serves as an oxygen gas rate-determining member. Therefore, by forming two different sensors on the porous alumina substrate, the air-fuel ratio can be detected in the wide range between $\lambda=1$ and the lean air-fuel ratio region with good accuracy and reliability.

According to an aspect of the air-fuel ratio detecting apparatus, the comparator/discriminator is arranged to be able to quickly discriminate a change from the fuel lean state to the fuel rich state since a high reference value is adapted. Therefore, spike noise generated upon the change from the fuel lean state to the fuel rich state can be eliminated.

According to another aspect of the air-fuel ratio detecting apparatus, the output signal adding section has an inverting adder, the input terminals of which are respectively connected to level regulators. The adder receives and adds the output signals from the current detector, the output signal from the comparator/discriminator, and a negative DC bias signal, thereby obtaining the desired single sensor output.

BRIEF DESCRIPTION OF THE DRAWINGS

FIGS. 15 to 17 are timing charts of outputs from a current detector 55 and a resistance detector 56 in the circuit of FIG. 14 when measuring conditions vary, in which FIG. 15 shows waveforms obtained when a voltage is continuously supplied to the limiting electric current type oxygen sensor portion 51 in the rich and lean states, FIG. 16 shows waveforms obtained when the voltage is supplied to the limiting electric current oxygen sensor portion 51 only when the output from the resistive type oxygen sensor portion 52 detects a lean state, wherein a reference resistance is set to be $10^5\Omega$, and FIG. 17 shows the waveforms of FIG. 16 when the reference resistance is set to be $10^7$;

DETAILED DESCRIPTION OF THE PREFERRED EMBODIMENTS

The present invention will be described in detail with reference to the preferred embodiments.

A. Sensor Portion

Figure 1A:
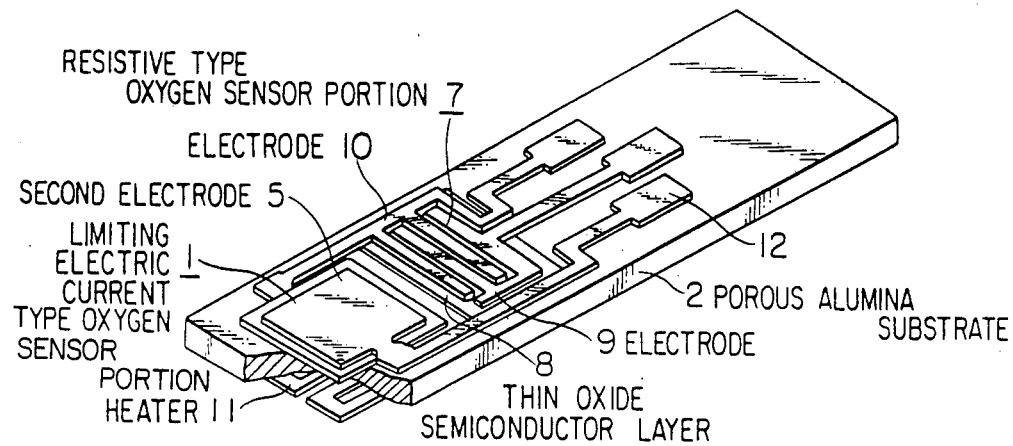
FIG. 1(a) and 1(b) are perspective view and a sectional view of an air-fuel ratio sensor according to an embodiment of the present invention.
Figure 1B:
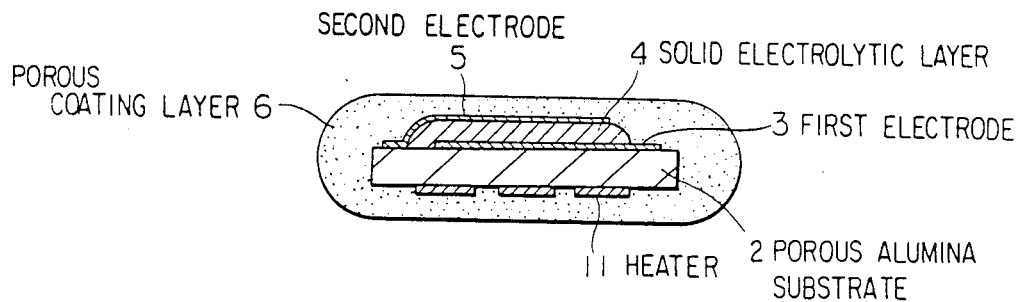

FIGS. 1(a) and 1(b) show the basic structure of an air-fuel ratio sensor according to an embodiment of the present invention. FIG. 1(a) is a perspective view showing the outer appearance of the air-fuel ratio sensor, and FIG. 1(b) is a sectional view of a limiting electric current type oxygen sensor portion 1 in the air-fuel ratio sensor. A limiting electric current oxygen sensor 1 serves as a portion for detecting lean regions. A first electrode 3, a solid electrolytic layer 4, and a second electrode 5 are sequentially formed on a porous alumina substrate 2 having a porosity of 2 to 40% and a pore diameter of 0.02 μm to 1.2 μm. The first electrode is made of platinum (Pt) and has a high gas permeability. The solid electrolytic layer 4 is made of $(ZrO_2)_{0.9\text{-}2}(Y_2O_3)_{0.08}$, which has a predetermined crystal orientation, a thickness of 0.1 μm to 30 μm, and a good crystallinity. The second electrode 5 is also made of Pt with a high gas permeability. A resistive type oxygen sensor portion 7, acting as a sensor for detecting an excess air ratio $\lambda=1$, has a pair of interdigital electrodes 9 and 10 formed on one or both surfaces of an oxide semiconductor thin film 8, the resistance of which changes greatly in accordance with oxygen partial pressure. A heater 11 is formed on one surface of the porous substrate 2 to heat the sensor portions 1 and 7. The heater is preferably formed near the sensor portions. The overall structure of the sensor is covered with a porous coating layer 6 which carries a catalyst.

In order to clarify the experimental assumptions and effects of the structure of the sensor portions described above, the resistive type oxygen sensor portion and the limiting electric current type sensor portion will be described separately.

a. Resistive Type Oxygen Sensor Portion

Figure 2:
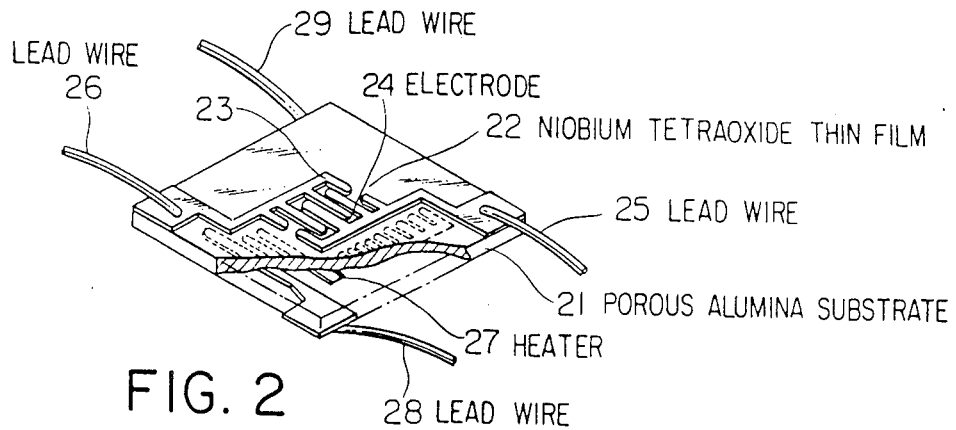
FIG. 2 is a perspective view of a conventional $\lambda=1$ sensor.
Figure 3:
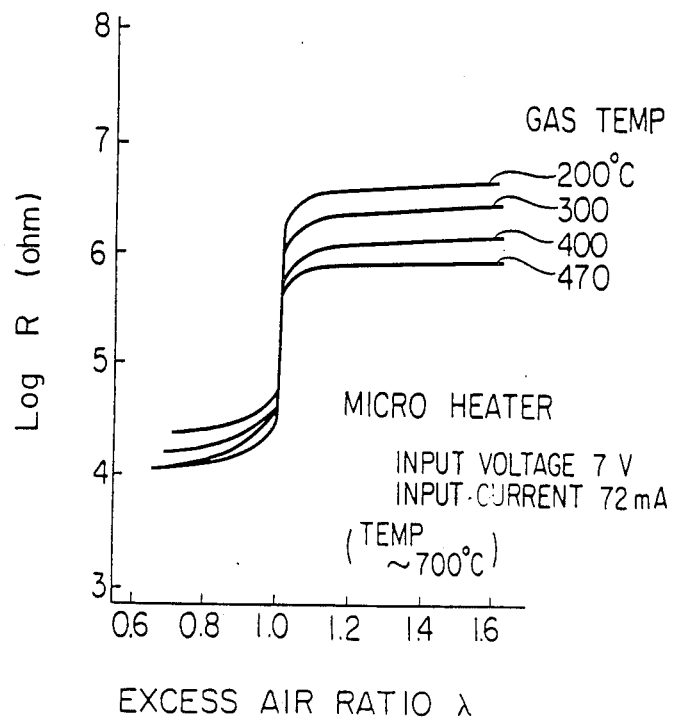
FIG. 3 is a graph showing the relationship between the resistance R and the excess air ratio $\lambda$ in the $\lambda=1$ sensor.

FIG. 2 shows the structure of a thin-film niobium tetraoxide ($Nb_2O_5$) oxygen sensor using $Nb_2O_5$ as an oxide semiconductor material for detecting $\lambda=1$. A niobium tetraoxide ($Nb_2O_5$) thin film 22 is formed on one major surface of a porous alumina ($Al_2O_3$) substrate 21, and interdigital electrodes 23 and 24 are formed on the film 22. Pt lead wires 25 and 26 are connected to the electrodes 23 and 24. A Pt heater 27 is formed on the other major surface of the $Al_2O_3$ substrate 21. Lead wires 28 and 29 are connected to two ends of the heater 27. A porous catalyst layer is formed on the surface of the sensor portions to prevent deposition of noncombusted material. In this case, a thickness and an average pore diameter are selected for the catalyst layer such that the ratio of thickness to average pore diameter falls within the range of 50 to 3,000. The catalyst component carried by the catalyst layer consists of one material selected from the group consisting of palladium (Pd), rhodium (Rd), platinum (Pt), and a mixture thereof. The catalyst carrying content is preferably 0.001 wt % to 50 wt %. As shown in FIG. 3, the air-fuel ratio sensor is free from variations in gas temperature and has characteristics wherein its resistance changes abruptly at $\lambda = 1$. In this embodiment, $Nb_2O_5$ is used as a sensor material. However, $TiO_2$, $CeO_2$, $SnO_2$ or the likely may be used equally effectively in place of $Nb_2O_5$.

b. Limiting Electric Current Type Oxygen Sensor Portion b-1. Porous Substrate as Oxygen Gas Diffusion Resistor

An oxygen gas diffusion resistor or oxygen gas rate-determining member in a limiting electric current type oxygen concentration sensor conventionally comprises:

(1) a porous coating layer formed by plasma flame spraying on the entire surface of a fine solid electrolyte having an anode and a cathode, or (2) a cover with pores formed on one electrode of the solid electrolyte to control diffusion of the oxygen gas (housing method).

Figure 4:
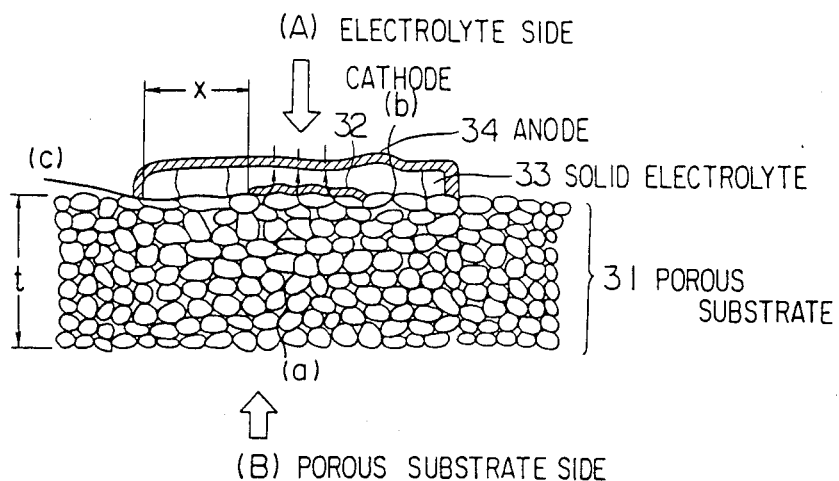
FIG. 4 is an illustrative representation showing a section of a limiting electric current type sensor on a porous substrate and oxygen gas paths.

As opposed to these diffusion resistors, a new oxygen gas diffusion resistor according to the present invention comprises:

(3) a porous substrate 31 in the limiting electric current type oxygen sensor (FIG. 4), on which an electrode (cathode) 32, a solid electrolyte 33, and an electrode (anode) 34 are sequentially stacked. Oxygen gas flow paths in the porous substrate 31 are represented by (a), (b), and (c) in FIG. 4. When positive and negative constant voltages are applied to the anode 34 and the cathode 32, respectively, the oxygen gas passes along the following paths.

(a) The oxygen gas reaches the cathode 32 through the pores of the substrate 31 and is ionized. Oxygen ions pass through the solid electrolyte 33 and reach the anode 34. The oxygen ions are converted by the anode 34 to oxygen gas, which is then emitted in the outer atmosphere.

(b) The anode 34 and the solid electrolyte 33 are porous. The oxygen gas reaches the cathode 32 through the anode 34 and the solid electrolyte 33. The gas is ionized at the interface between the cathode 32 and the solid electrolyte 33, and the resulting oxygen ions reach the anode 34 through the solid electrolyte 33. The oxygen ions are converted by the anode 34 to oxygen gas, which is then emitted in the outer atmosphere.

(c) The oxygen gas reaches the cathode 32 through an interface between the solid electrolyte 33 and the porous substrate 31. The oxygen gas is ionized by the cathode 32, and the oxygen ions reach the anode 34 through the solid electrolyte 33. The ions are converted to oxygen gas by the anode 34.

In this case, the porous substrate 31 serves as a gas diffusion resistor, and only path (a) is used. The oxygen gas reaching the cathode also passes along the paths (b) and (c) in accordance with design precision. The gas components passing along the paths (b) and (c) are mixed in with the component passing along the path (a).

Assume that the thickness of the porous substrate is given as t and the distance between the end of the solid electrolytic thin film formed on the porous substrate and the end of the cathode 32 is given as x. Test samples with different x/t ratio were prepared. Oxygen gas was supplied alternately from the electrolyte side (A) and the porous substrate side (B), while oxygen gas concentration was varied to obtain limiting electric currents (FIG. 4) from the cathode 32 to the anode 34. In this case, a model calculation expression was established, and the influence of oxygen gas components diffused to the cathode 32 through the paths (c) and (b) was examined. Results are shown in Table 1.

TABLE 1

| | Relationship Between x/t and y and Evaluation | | | | | | | | | |
|---|---|---|---|---|---|---|---|---|---|---|
| x/t | 0.5 | 0.75 | 1 | 1.25 | 1.50 | 1.75 | 2.0 | 2.5 | 3 | 4 |
| y(%) | 90 | 60 | 40 | 20 | 10 | 5 | 5 | 5 | 5 | 5 |
| E-valuation | x | x | Δ | o | o | o | o | o | o | o |

As is apparent from Table 1, when the x/t value is 0.75 or less, the influence of oxygen gas components passing along the paths (c) and (b) is large. When x/t is 1.75 or more, the influence of the components through the paths (c) and (b) is very small. Therefore, it was found that a practical range for x/t would be 0.75 or more.

b-2 Dielectric Breakdown of Solid Electrolytic Film

In order to premeate oxygen gas as ions through the solid electrolyte, the conventional sensor requires a dense solid electrolytic film which does not allow permeation of oxygen gas. However, extensive studies showed that it is difficult to obtain a film which does not allow permeation of oxygen gas but does allow permeation of oxygen ions, when such a film is formed by a physical process on the porous substrate. Most solid electrolytic films formed on porous substrates are porous electrolytic films more subject to dielectric breakdown than fine films. Therefore, the relationship between dielectric breakdown of the solid electrolytic film and the porosity and pore diameter of the porous substrate was examined.

The pore diameter of the porous substrate was varied from $0.01\mu$ to $2.3\mu$ while the porosity thereof was fixed at 15%. Also, the porosity was varied from 0.2% to 60% while the pore diameter was fixed at 0.5 $\mu m$. Under these conditions, a Pt electrode with a thickness of 1 $\mu m$, a solid electrolyte ($ZrO_2 + Y_2O_3$) with a thickness of 4 $\mu m$, and a Pt electrode with a thickness of 1 $\mu m$ were sequentially stacked on the porous substrate to prepare a number of limiting electric current oxygen sensors.

A voltage of about 0.75 V was applied to each sample sensor at an $O_2$ was concentration of 20% using an $N_2-O_2$ gas system while the sample was heated to a temperature of about 700° C. The relationship between dielectric breakdown and pore diameter and the relationship between dielectric breakdown and porosity are summarized in Tables 2 and 3, respectively.

several angstroms. It is therefore theoretically possible to decrease the electrical resistance of the electrolyte to

TABLE 2

Relationship Between Pore Diameter and Dielectric Breakdown

| | Pore Diameter (μm) | | | | | | | |
|---|---|---|---|---|---|---|---|---|
| | 0.01 | 0.02 | 0.07 | 0.1 | 0.3 | 0.7 | 1.2 | 1.7 | 2.3 |
| Dielectric Breakdown | Occurred | Partial breakdown | Not occurred | Not occurred | Not occurred | Not occurred | Slight breakdown | Occurred | Occurred |

TABLE 3

Relationship Between Porosity and Dielectric Breakdown

| | Porosity (%) | | | | | | | |
|---|---|---|---|---|---|---|---|---|
| | 0.2 | 0.5 | 2 | 5 | 10 | 30 | 40 | 50 | 60 |
| Dielectric Breakdown | Occurred | Occurred | Partial breakdown | Not occurred | Not occurred | Not occurred | Not occurred | Occurred | Occurred |

As is apparent from Table 2, when the pore diameter is 0.02 μm or less, oxygen gas tends not to be diffused in the porous substrate, so that the solid electrolytic film peels from the substrate. When pore diameter falls within the range of 0.02 μm to 1.2 μm, short-circuiting does not occur. However, when the pore diameter is 1.2 μm or more, a large amount of oxygen gas is diffused in the substrate and reaches the cathode. A large number of oxygen ions flow through the solid electrolyte, resulting in dielectric breakdown. Therefore, a practical pore diameter range would be 0.2 μm to 1.2 μm.

As is apparent from Table 3, when porosity is 2% or less, oxygen gas does not flow through the porous substrate, and the solid electrolytic film peels from the substrate. When porosity exceeds 40%, dielectric breakdown occurs. Therefore, a practical porosity range would be 2 to 40%.

b-3 Film Thickness and Resistivity of Solid Electrolyte

Figure 5:
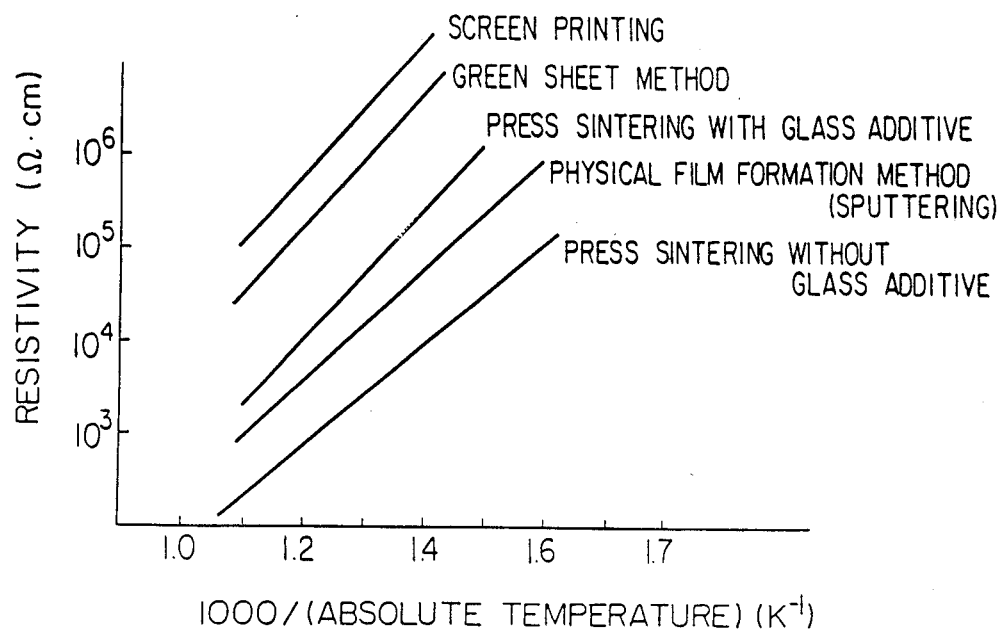
FIG. 5 is a graph showing the resistivity-temperature characteristics of solid electrolytes prepared by different fabrication methods.

Methods of forming a fine solid electrolytic film which allows permeation of only oxygen ions include sintering, the green sheet method, and screen printing. The physical thin film formation methods (e.g., sputtering, deposition, or CVD) are also available. The resistivity-temperature characteristics of the solid electrolytes ($ZrO_2 + Y_2O_3$) prepared by the above methods are shown in FIG. 5. As is apparent from FIG. 5, resistivity of the solid electrolyte ($ZrO_2 + Y_2O_3$) varies with each method. In order to obtain a dense solid electrolyte of high purity and good ion conduction, the electrolyte is preferably press-sintered without using a glass additive to accelerate sintering. As a result, the material must be sintered at a temperature of 2,000° C. for 2 to 3 hours at atmospheric pressure. With methods (e.g., press sintering, the green sheet method, or screen printing) using a glass additive, a sufficiently dense sintered body can be obtained at temperatures of 1,600° C. or less. However, since the additive is mixed in with the electrolyte, the resultant body has a high resistivity. According to a practical technique for decreasing electrical resistance of the sensor, the thickness of the solid electrolyte can be decreased. However, it is impossible to decrease the film thickness to 50 μm or less using the methods described above. On the other hand, a solid electrolytic thin film prepared by a physical method (e.g., sputtering, deposition, or CVD) has good crystallinity and is denser than the sintered electrolytic film. In addition, no glass component is added, so the resultant film has a low resistivity. Furthermore, the thickness of the electrolytic film can vary from several tens of microns to 1/100 to 1/500 that of a conventional sintered electrolytic film by decreasing the film thickness.

In practice, the degree of reduction in film thickness is limited in accordance with film quality. When film quality is poor, the resistance of the solid electrolyte cannot be decreased, and the film is unstable. Therefore, it is important to prepare a stable crystalline film of good quality and to determine an optimal film thickness range. The relationship between the thickness and resistance of a solid electrolytic thin film at an ambient temperature of 700° C. was examined, and results are shown in FIG. 6.

Figure 6:
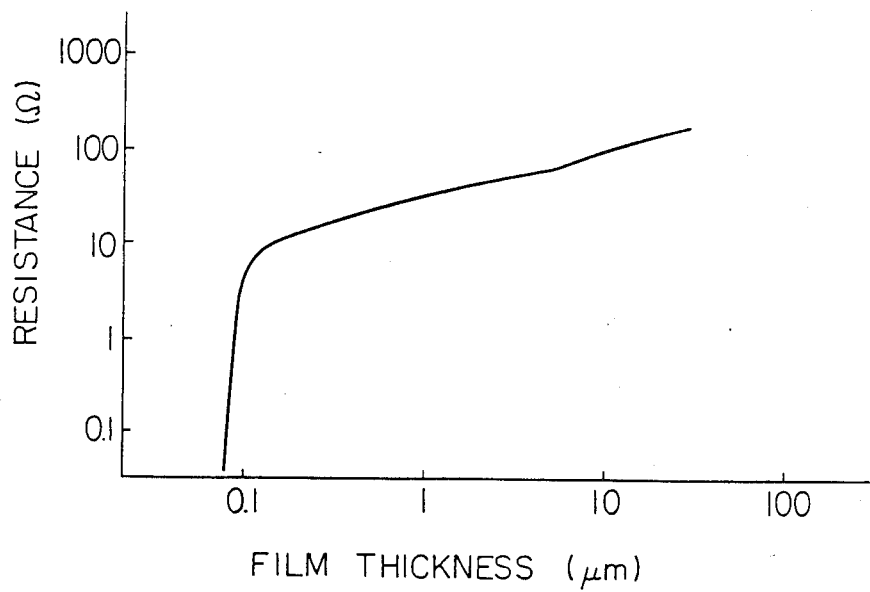
FIG. 6 is a graph showing the resistance of the electrolyte as a function of film thickness.

Referring to FIG. 6, when the thickness of the solid electrolyte is 0.1 μm or less, its resistance is rapidly decreased, which cause short-circuiting. However, when the film thickness is 0.1 μm or more, the film thickness is proportional to the resistance. In other words, when the film thickness is increased, the resistance is increased accordingly. Therefore, a minimum film thickness is 0.1 μm or more. Furthermore, from the viewpoint of practical applications, film deposition or sputtering rate by a physical process is as low as several hundreds of angstroms per minute. When the film thickness is increased, the resistance is increased accordingly, so that a detection current is decreased. As a result, an optimum film thickness range is 0.1 μm to 30 μm.

b-4 Film Quality of Solid Electrolyte

Figure 7:
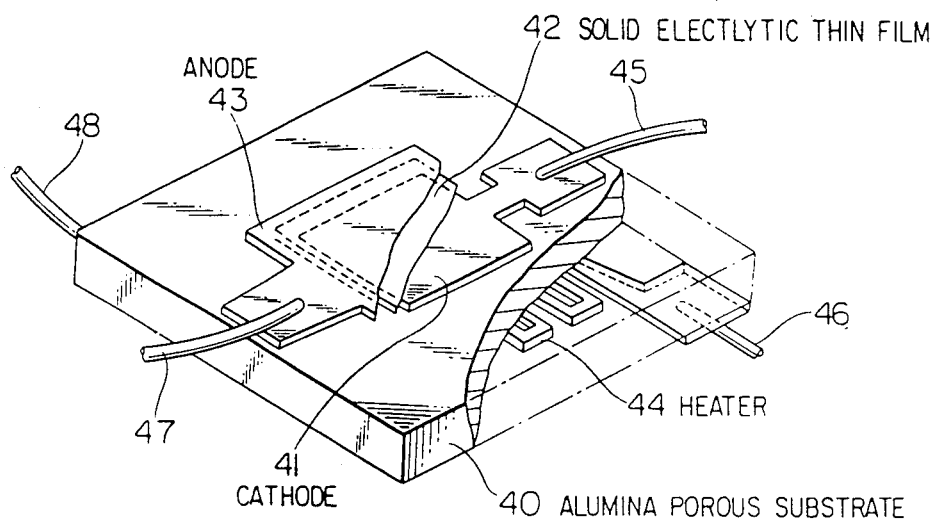
FIG. 7 is a perspective view of a conventional limiting electric current type sensor.

FIG. 7 shows a structure of a limiting electric current type oxygen sensor to which the present invention is applied. The quality of the solid electrolyte films is examined.

A cathode 41 of a Pt film, a solid electrolytic ($ZrO_2 + Y_2O_3$) thin film 42 and an anode 43 of a Pt film are sequentially formed on one major surface of an alumina porous substrate 40 containing $Al_2O_3$ as a major constituent, thereby constituting a sensor portion. A zig-zag patterned heater 44 of a Pt thin film is formed on the other major surface of the alumina porous substrate 40 to heat the sensor portion. The resultant structure is covered with a porous coating layer and is thus mechanically protected. Pt lead wires 45, 46, 47 and 48 having a diameter of 50 μm are connected to the heater 44, the anode 43 and the cathode 41.

In the limiting electric current type oxygen sensor using the solid electrolytic thin film, it is important to determine how an electrolytic thin film of good crystallinity and stability is formed. Preferably, the resultant film has a low electric resistance and dense texture and allows conduction of only oxygen ions therethrough. In order to determine conditions which satisfy these requirements, the following experiment was made.

A solid electrolyte ($ZrO_2+Y_2O_3$) of a thickness of about 2 μm to 4 μm was formed on an upper surface of a quartz substrate (dimensions of 20×20×0.5 mm) by using a high-rate sputtering apparatus under the following conditions:

Distance between the target and the substrate: 60 to 70 mm

Sputtering Atmosphere
  (1) Ar flow rate: 20 cc/min
      Pressure: $4\times10^{-3}$ Torr
  (2) 10%—$O_2$/Ar flow rate: 1 cc/min
      Pressure: $4\times10^{-3}$ Torr
  (3) Switch from the atmosphere given by
      Ar flow rate: 20 cc/min
      to the atmosphere given by
      Ar flow rate: 20 cc/min
      10%—$O_2$/Ar flow rate: 1 cc/min
  (4) Switch from the atmosphere given by
      Ar flow rate: 20 cc/min
      10%—$O_2$/Ar flow rate: 1 cc/min
      to the atmosphere given by
      Ar flow rate: 20 cc/min Input Power: 300 W Reflected Wave Power: 0 W Input Current: 0.2 A Substrate Temperatures: 20° C., 200° C., 500° C., 700° C. and 1,000° C.

Sputtering Time: 4 to 8 hours

X-ray diffraction analysis was performed for the sputtered $ZrO_2+Y_2O_3$ thin films, and results were as given in Table 4. Different crystal structures are found to be obtained in accordance with different gas atmospheres and substrate temperatures.

TABLE 4

| Sputtering Atmosphere | Substrate Heating Temperature (°C.) | Crystal Orientation |
|---|---|---|
| 1 Ar gas | 200 or less | amorphous |
| | 200 to 500 | [111] + [200] fiber texture |
| | 500 or more | weak [111] fiber texture |
| 2 Ar + $O_2$ gas | 200 or less | amorphous |
| | 200 to 350 | weak [111] fiber texture |
| | 350 or more | strong [111] fiber texture |
| 3 Ar gas → Ar + $O_2$ gas | room temperature (water cooling) to 1000 | [111] + [200] + [220] + [311] fiber texture |
| 4 Ar + $O_2$ gas → Ar gas | room temperature (water cooling) to 1000 | [111] + [200] + [220] + [311] fiber texture |

Figure 8:
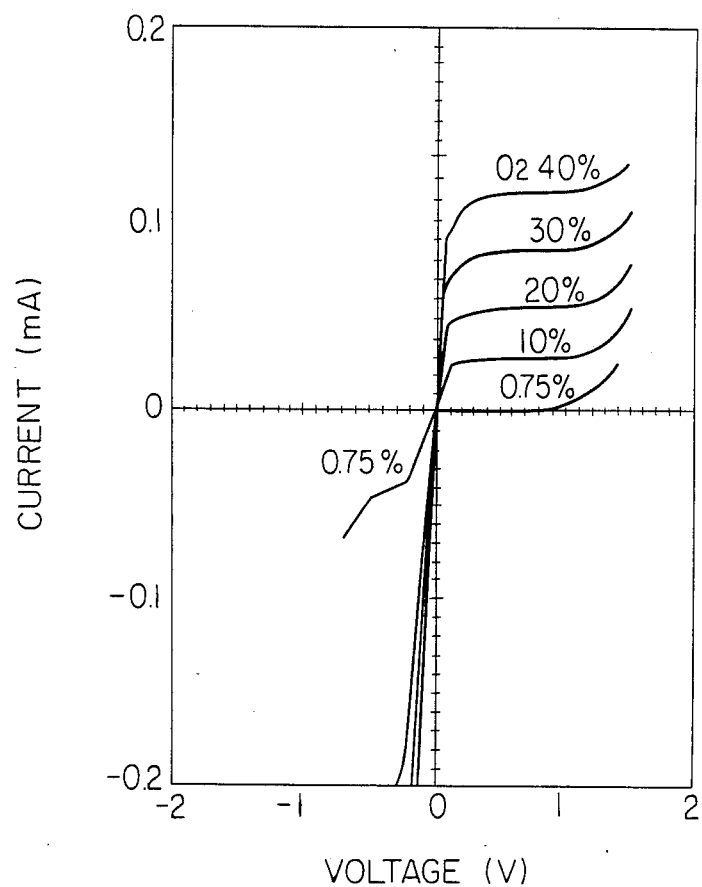
FIG. 8 is a graph showing the current-voltage characteristics of the limiting electric current type sensor when oxygen concentration is used as a parameter.
Figure 9:
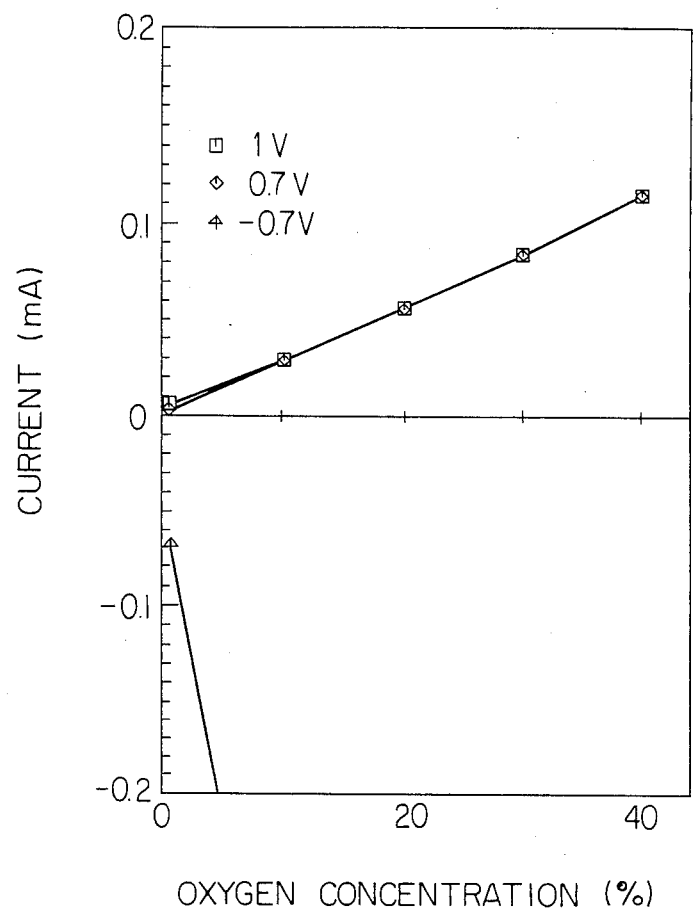
FIG. 9 is a graph showing the relationship between the limiting electric current and the oxygen gas concentration.

The prepared films were annealed at a temperature of 1,000° C. and atmospheric pressure for 3 hours. The annealed films were then subjected to the X-ray diffusion test again to check changes in film structures before and after annealing. In an amorphous film prior to annealing, crystal growth partially occurred along the [111]+[220] direction. However, once crystal growth occurred along a specific direction, reannealing did not change the film quality. By using each film given above, a multilayer sensor shown in FIG. 7 was prepared. Current-voltage characteristics of the prepared sensors were measured by using as a parameter the $O_2$ gas concentration in the $N_2$ gas. Results are shown in FIG. 8. Furthermore, oxygen concentration-current characteristics of the sensors were measured while a constant voltage of 0.75 V was applied to the sensors. The sensors were kept at a constant temperature of 700° C. Results are shown in FIG. 9. The characteristics of the sensors did not greatly change in accordance with the film formation conditions. As the initial characteristics, the output current is proportional to an increase in oxygen concentration. In order to test stability of these sensors, changes in output currents as a function of time were measured when the sensors were kept at a constant temperature of 700° C. and in the outer atmosphere. Results are summarized in Table 5.

TABLE 5

| | Stability Test Results of Different Films | | | | |
|---|---|---|---|---|---|
| | Initial | After 50 Hours | After 200 Hours | After 500 Hours | Evaluation |
| Amorphous Films | 0.8 mA | 20% output electric current increase | 40% output electric current increase | 64% output electric current increase | x |
| Weak [111] Fiber Texture Orientation Film | 1.1 mA | 3% output electric current increase | 4% output electric current increase | 5% output electric current increase | o |
| Strong [111] Fiber Texture Orientation Film | 1.3 mA | 2% output electric current increase | 3% output electric current increase | 3% output electric current increase | o |
| [111] + [220] Fiber Texture Orientation Film | 1.2 mA | 1% output electric current increase | 1% output electric current increase | 1% output electric current increase | o |
| [111] + [200] + [220] + [311] Fiber Texture Orientation Film | 1.2 mA | 1% output electric current increase | 1% output electric current increase | 1% output electric current increase | o |

According to the results shown in Table 5, an output current from an amorphous solid electrolytic film is increased over time, and deterioration over time is significant. However, in a solid electrolytic thin film having a specific crystal growth direction, changes in output current are small and operation is thus stable.

As is apparent from the above description, a film having a given crystal orientation must be used as an oxygen sensor material.

In this embodiment, $ZrO_2+Y_2O_3$ is used as an electrolytic thin film material. However, an electrolytic thin film may be formed by adding a stabilizer (e.g., $Yb_2O_3$, $Gd_2O_3$, MgO, CaO or $Sc_2O_3$) to $ZrO_2$. Alternatively, an electrolytic thin film may be formed using as a target material a material obtained by adding $Y_2O_3$, $Er_2O_3$ or $WO_3$ to $Bi_2O_3$.

B. Air-Fuel Ratio Detecting Apparatus

Figure 10:
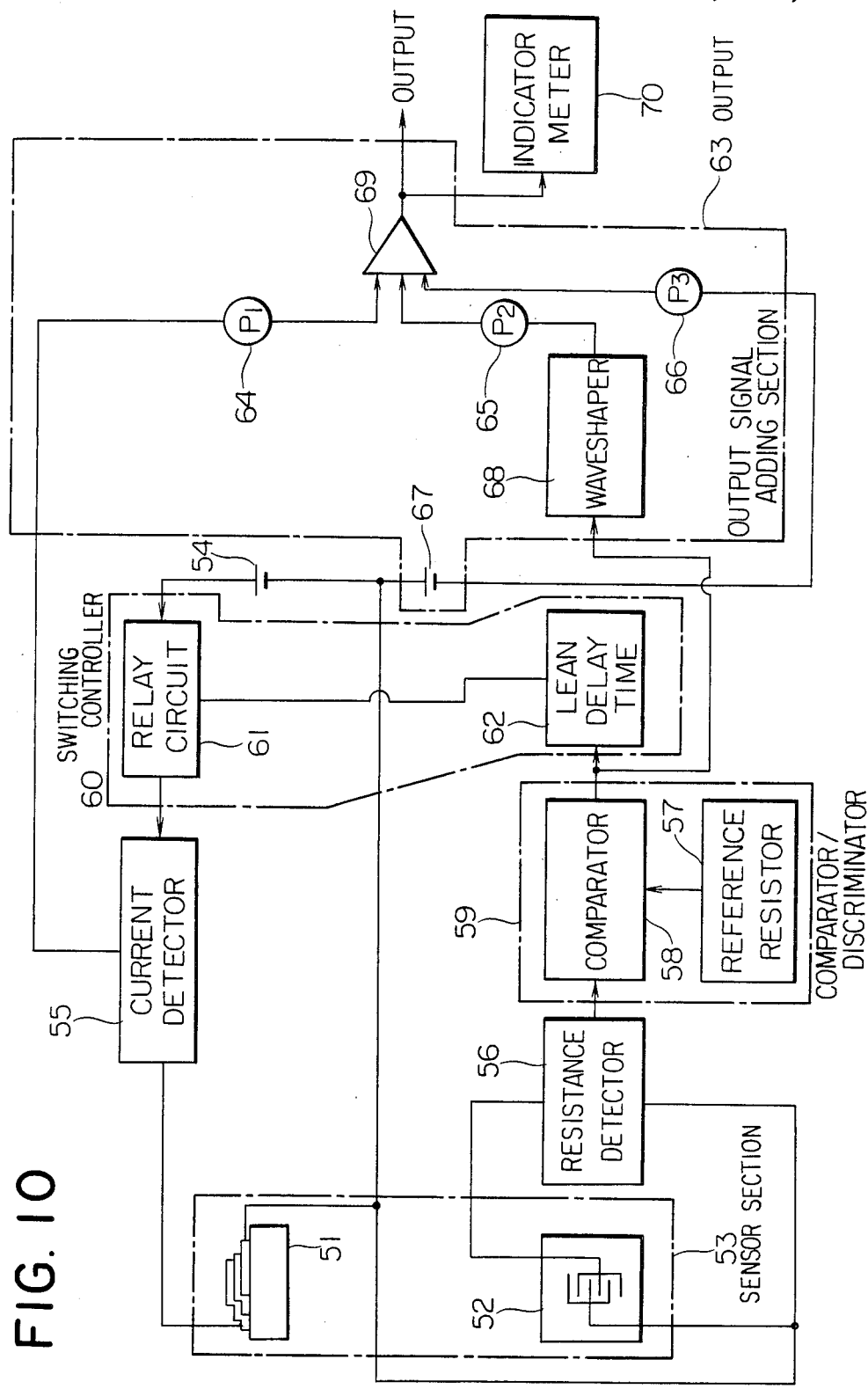
FIG. 10 is a block diagram of an air-fuel ratio detecting apparatus according to another embodiment of the present invention.

FIG. 10 shows an air-fuel ratio detecting apparatus including the air-fuel ratio sensor and a processing circuit for driving the air-fuel ratio sensor and processing an output therefrom according to another embodiment of the present invention.

The air-fuel ratio detecting apparatus comprises: an integral sensor section 53 having a limiting electric current type oxygen sensor portion 51 and a resistive type oxygen sensor portion 52; a limiting electric current measuring voltage source 54 for generating a voltage applied to the limiting electric current type oxygen sensor portion 51; a current detector 55 for detecting a current flowing through the limiting electric current type oxygen sensor portion 51 upon an application of the voltage thereto; a resistance detector 56 for detecting a resistance of the resistive type oxygen sensor portion 52; a comparator/discriminator 59, having a comparator 58 for comparing an output from the resistance detector 56 and the value of a reference resistor 57, for discriminating whether or not the air-fuel ratio represents a fuel rich or fuel lean state; a switching controller 60 for connecting the limiting electric current measuring voltage source 54 to the limiting electric current type oxygen sensor portion 51 when a predetermined period of time has elapsed after the fuel rich state changes to the fuel lean state, and for disconnecting the limiting electric current measuring voltage source 54 from the limiting electric current type oxygen sensor portion 51 when the fuel lean state changes to the fuel rich state; an output signal adding section 63 for adding an output signal from the limiting electric current oxygen sensor portion 51 and an output signal from the resistive type oxygen sensor portion 52 and generating a signal representing an air-fuel ratio; and an indicator 70 for indicating the output from the output signal adding section 63.

The switching control 60 comprises a relay circuit 61 for connecting/disconnecting the limiting electric current measuring voltage source 54 to/from the limiting electric current type sensor portion 51, and a lean delay time circuit 62 for delaying an output from the comparator/discriminator 59 by a predetermined period and supplying a delayed signal as a control signal to the relay circuit 61.

The output signal adding section 63 has an inverting adder 69, input terminals of which are respectively connected to potentiometers 64, 65 and 66 serving as level regulators. The inverting adder 69 adds the output signal from the current detector 55, the output signal from the comparator/discriminator 59 and a DC bias signal from a negative DC bias current source 67.

The signal from the comparator/discriminator is shaped by a wave shaper 68, and a waveshaped signal is supplied to the inverting adder 69.

The features of the air-fuel ratio detecting apparatus of this embodiment will be described in detail.

a. Noise Reduction

Figure 11:
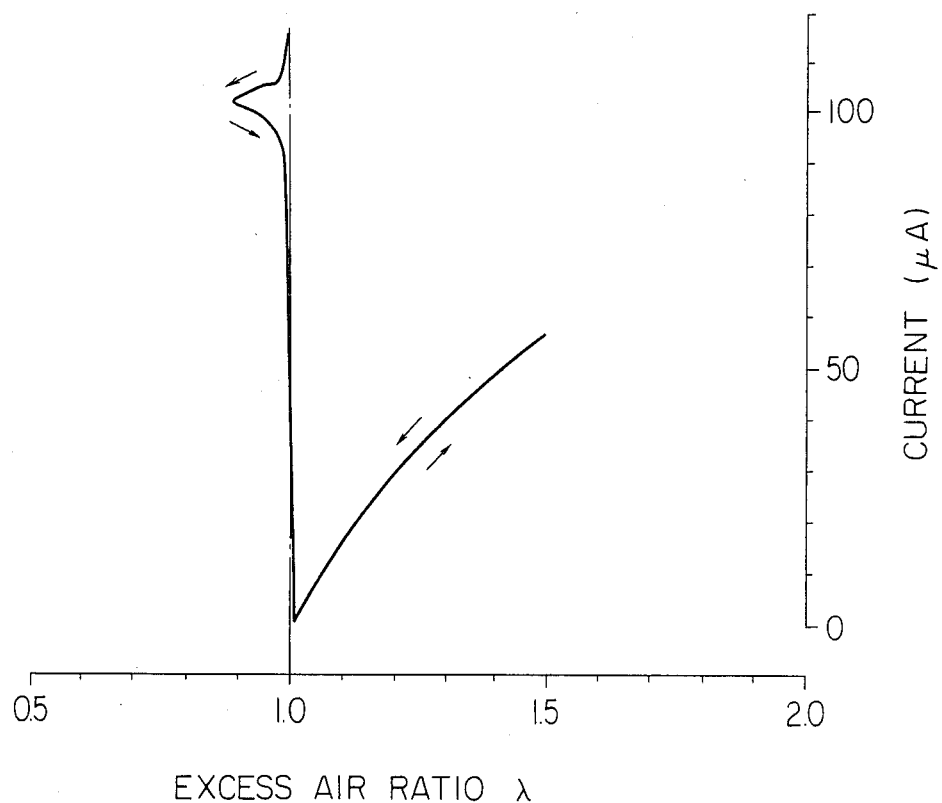
FIG. 11 is a graph showing excess air ratio-electric current characteristics for explaining the current flowing through a limiting electric current type oxygen sensor portion 51 as a function of the excess air ratio $\lambda$.

The current flowing in the limiting electric current type oxygen sensor portion 51 as a function of the excess air ratio λ is shown in FIG. 11. As is apparent from FIG. 11, the excess air ratio λ is proportional to the current when the excess air ratio λ is larger than 1 (i.e., in the lean fuel region).

However, in the region (i.e., the rich fuel region) where λ is smaller than 1, the current flows irrespective of the excess air ratio λ.

When the current is measured to calculate the excess air ratio λ, two λ values exist for a single current. These characteristics are called two-valued function characteristics which are undesirable for the sensor.

The relay circuit 61 is arranged to solve the problem described above in the embodiment of the present invention.

Figure 12:
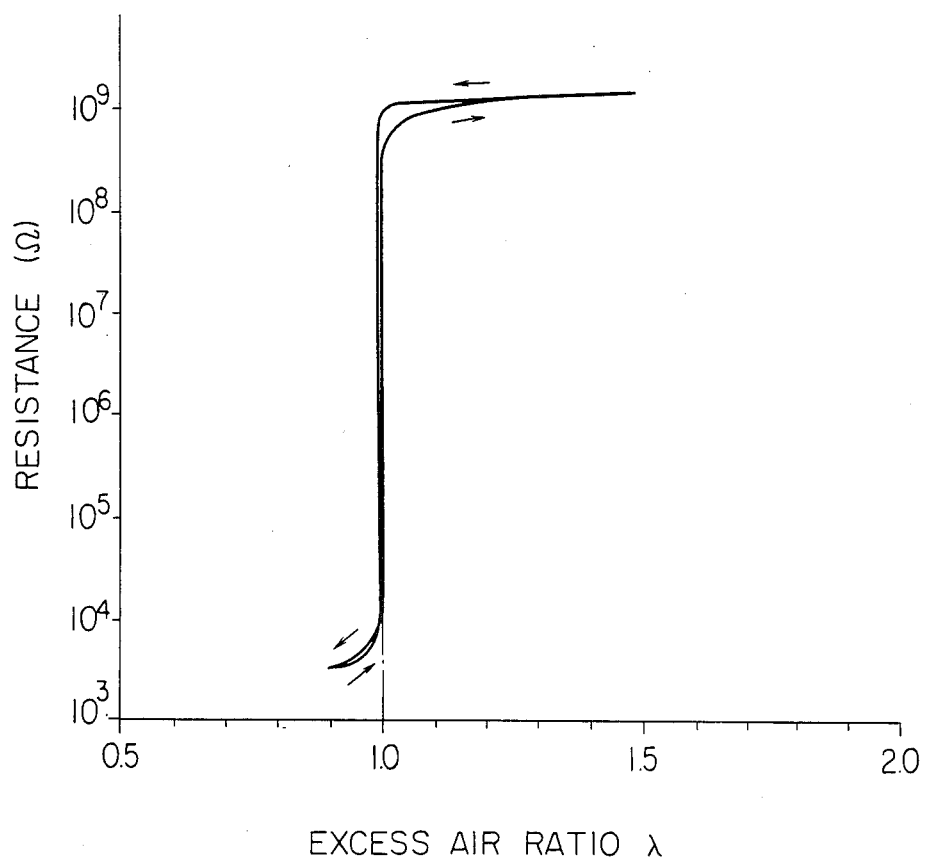
FIG. 12 is a graph showing resistance-excess air ratio characteristics for explaining the resistance of the resistive type oxygen sensor portion 52 as a function of excess air ratio $\lambda$.

FIG. 12 shows the characteristics of the oxygen sensor portion of an oxide semiconductor type in the air-fuel sensor. As is apparent from FIG. 12, the resistance of this sensor portion is abruptly changed at λ=1. The resistance is detected by the resistance detector 56, and an output therefrom is compared by the comparator 58 with a reference resistance (e.g., $10^6$ Ω), thereby discriminating the lean or rich state. Only when the comparator 58 determines the lean state, the voltage is applied to the limiting electric current type oxygen sensor portion 51. However, when the rich state is detected, the limiting electric current type oxygen sensor portion 51 is deenergized, thereby solving the problem presented by the two-valued function. The relay circuit 61 controls to energize or deenergize the limiting electric current type oxygen sensor portion 51.

Figure 13:
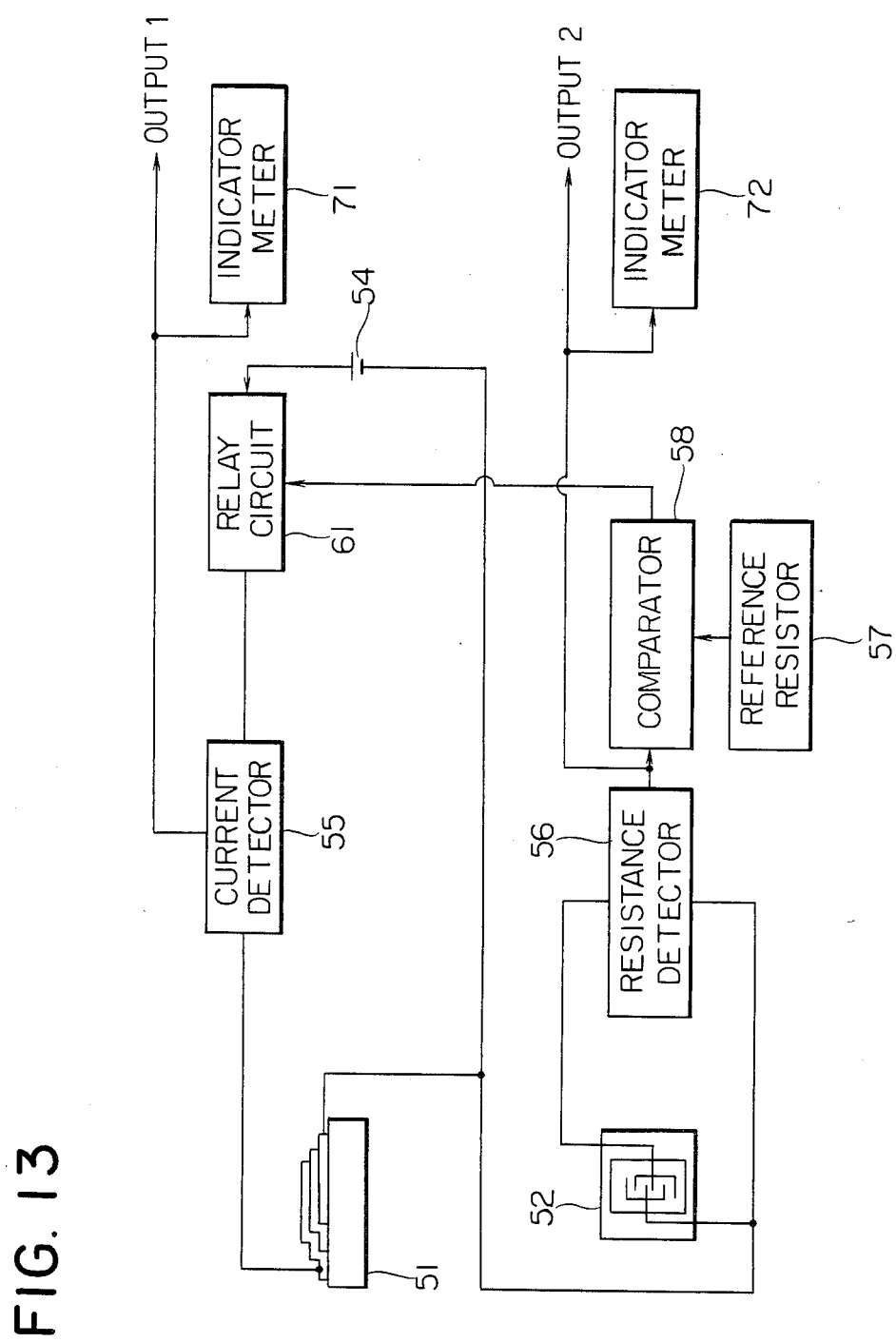
FIG. 13 is a block diagram of a circuit for causing the limiting electric current type oxygen sensor portion to operate only in the lean state.
Figure 14:
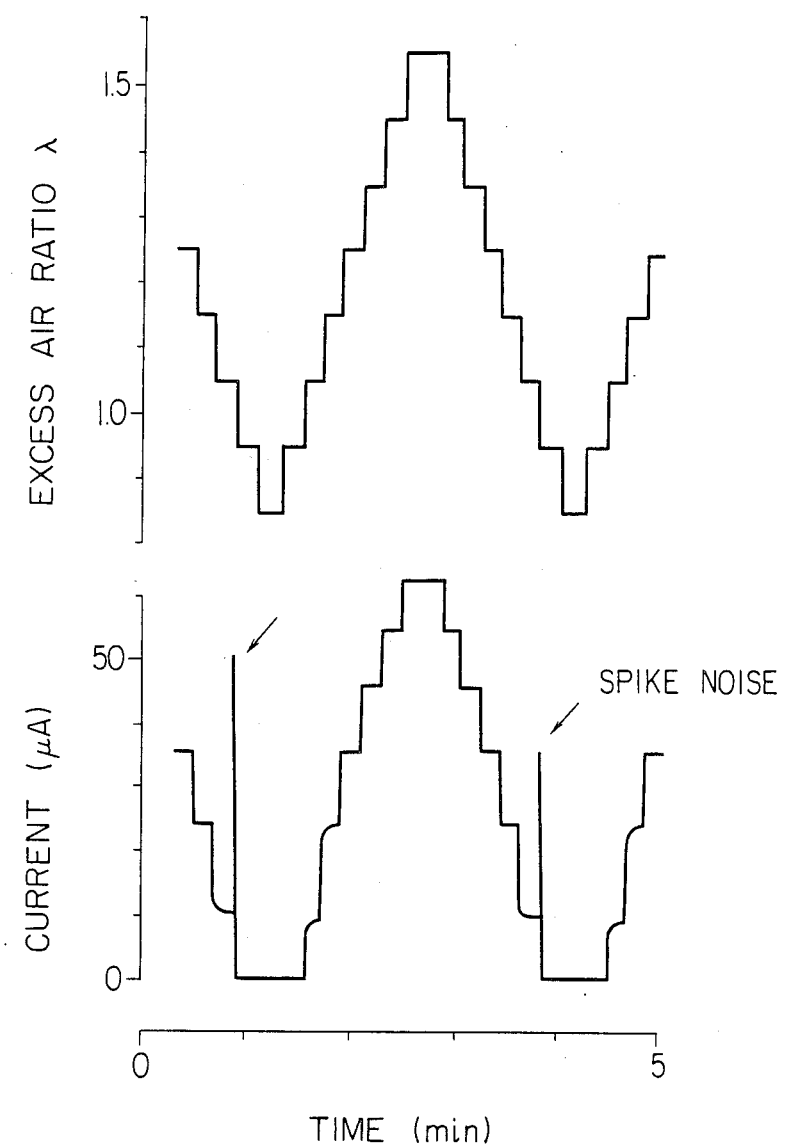
FIG. 14 is a graph showing output current changes detected by the circuit of FIG. 13 when the excess air ratio $\lambda$ is changed as a function of time.

In this manner, the solution to the problem of the two-valued function has been described with reference to the circuit arrangement of FIG. 13 wherein the measuring voltage is supplied to the limiting electric current type oxygen sensor portion 51 in only the lean state. FIG. 14 shows test results of the circuit in FIG. 13. In this case, the reference resistance varies between $10^5$ Ω and $10^{10}$ Ω. Even if any reference resistance falling within the above range is used, the current supply stops upon detection of the rich state. Therefore, it is readily understood that the circuit of FIG. 13 is properly operated.

When the graph is examined in detail, impulse spike noise is generated during switching from the lean state to the rich state. In this case, since the excess air ratio is shifted stably, spike noise is found to be caused by the sensor section.

Figure 15:
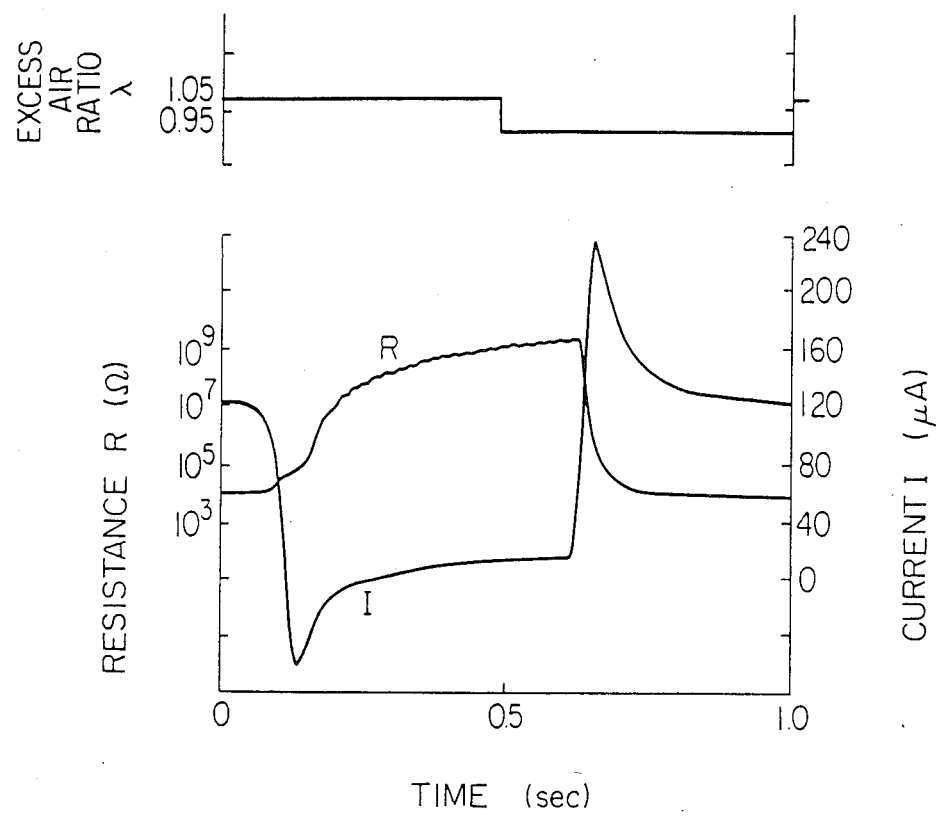
Figure 16:
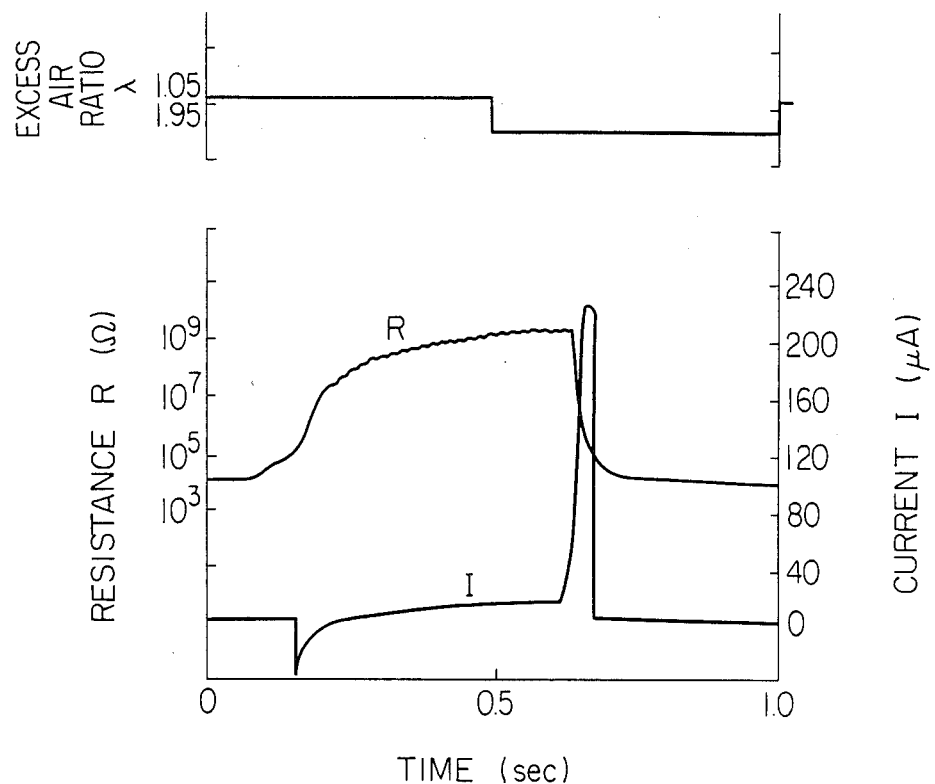
Figure 17:
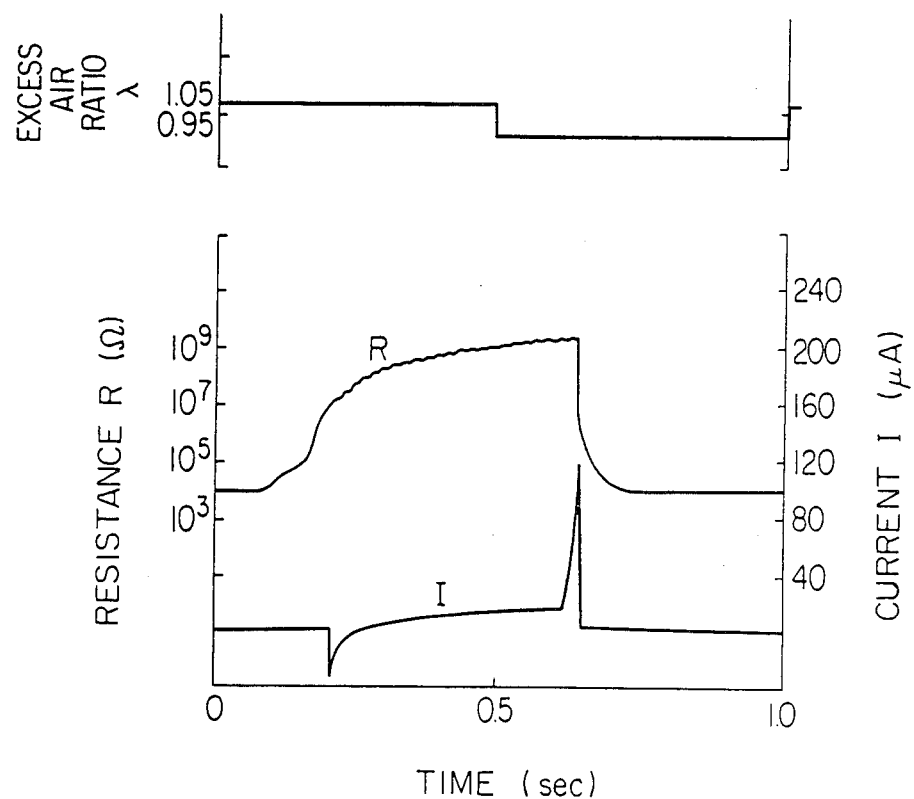

In order to solve this problem, the waveforms observed at an oscilloscope are shown in FIGS. 15 to 17.

FIG. 15 shows a waveform when the voltage is continuously supplied to the limiting electric current type oxygen sensor portion 51 in both the rich and lean states. A current flowing 0.4 seconds after the lean state (λ=1.05) is established corresponds to the oxygen concentration. When the rich is set, a current larger then this current flows. In addition, a current peak appears at switching.

FIG. 16 shows a waveform when the reference resistance is set to $10^5$ Ω, the resistance of the oxide semiconductor type oxygen sensor portion is less than $10^5$ Ω and, the limiting electric current type oxygen sensor portion 51 is deenergized and the rich state is detected.

As is apparent from FIG. 16, when the resistance of the portion 51 exceeds $10^5 \Omega$, the current flows through the limiting electric current type oxygen sensor portion. However, when the resistance is $10^5 \Omega$ or less, i.e., when the rich state changes to the lean state and the relay is energized, a negative current temporarily flows. At a moment immediately before the off state of the limiting electrc current type oxygen sensor portion, a positive pulse current flows therein.

FIG. 17 shows a waveform when the reference resistance is set to be $10^7 \Omega$. In this case, the spike current in the rich state flows in the same manner as in FIG. 16, but has magnitude and width smaller than those in FIG. 16. This is because the rich state is determined and the relay is immediately deenergized about 30 ms before the reference resistance is $10^6 \Omega$.

As is apparent from FIGS. 15 to 17, when the measuring voltage supplied to the sensor portion 51 is stopped before the spike current begins to flow in the limiting current type oxygen sensor portion 51, the spike current can be limited. This problem is associated with which one of the sensor portions is started first. The operation timing of the oxide semiconductor type oxygen sensor portion must be faster than that of the limiting electric current type oxygen sensor portion. In this case, as soon as the rich state changes to the lean state, the negative current spike has a large magnitude, so that this spike must be eliminated by an appropriate circuit. More particularly, the relay circuit must be delayed for a predetermined period of time after the lean detection signal is obtained. For this purpose, the lean delay time circuit 62 is arranged, as shown in FIG. 10.

Figure 18:
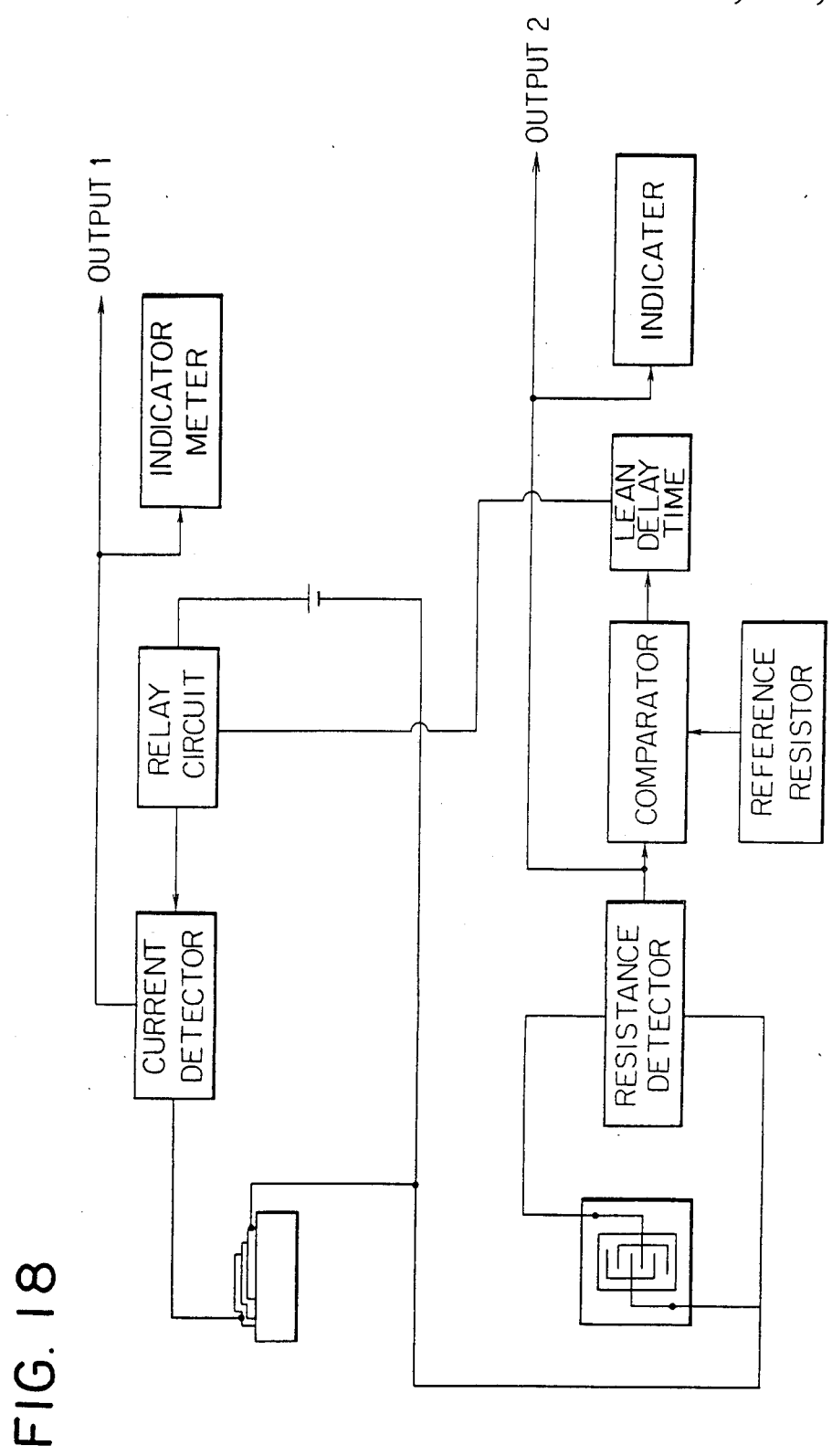
FIG. 18 is a block diagram of a circuit obtained by adding a lean delay time circuit to the circuit of FIG. 13.
Figure 23:
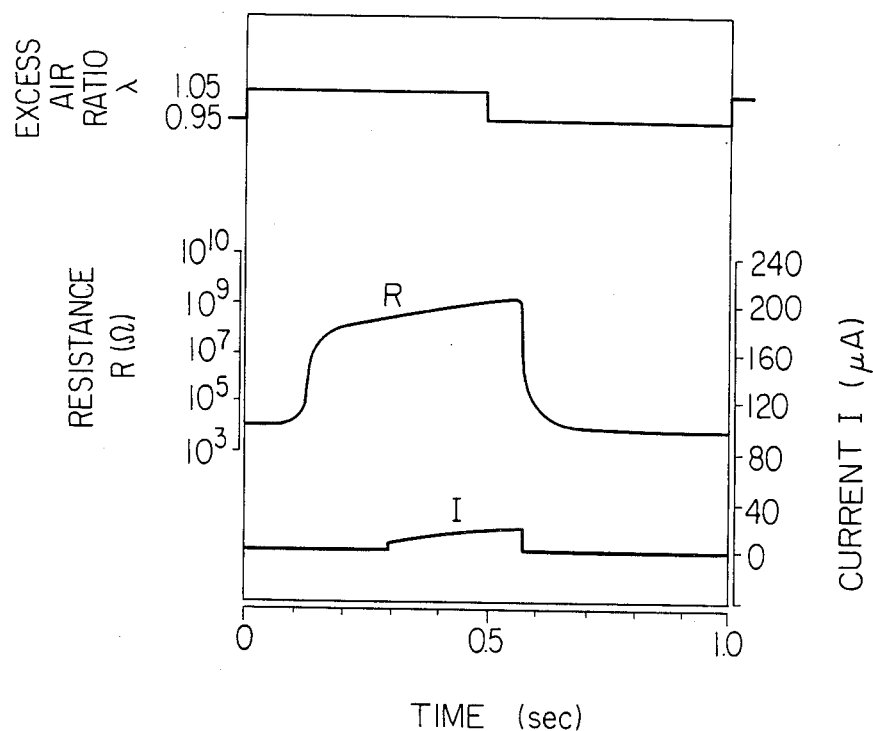
FIG. 23 is a graph showing signal waveforms when the lean delay time circuit is added and the response time o the oxide semiconductor type oxygen sensor portion is shortened.

A circuit shown in FIG. 18 is arranged to confirm the above effect. Results are shown in FIG. 23, and good characteristics can be thus obtained.

As described above, the change point from the lean state to the rich state is detected immediately by properly selecting the reference resistance for determining the lean or rich state on the basis of the output from the resistive type oxygen sensor portion. Thus, the spike noise appearing in the output from the limiting electric current type oxygen sensor portion upon switching from the lean state to the rich state can be eliminating. In addition, the lean delay time circuit (a delay time of 300 ms) is arranged to operate the limiting electric current type oxygen sensor portion only in the lean state, so that spike noise can be eliminated, thereby achieving excellent air-fuel ratio detection.

b. Addition of Output Signals from Both Sensor Portions

Referring to FIGS. 13 or 18, an output (output 1) from the limiting electric current type oxygen sensor portion is independent of an output (output 2) from the resistive type oxygen sensor portion.

Two independent outputs require a complex, expensive air-fuel control circuit.

Figure 19:
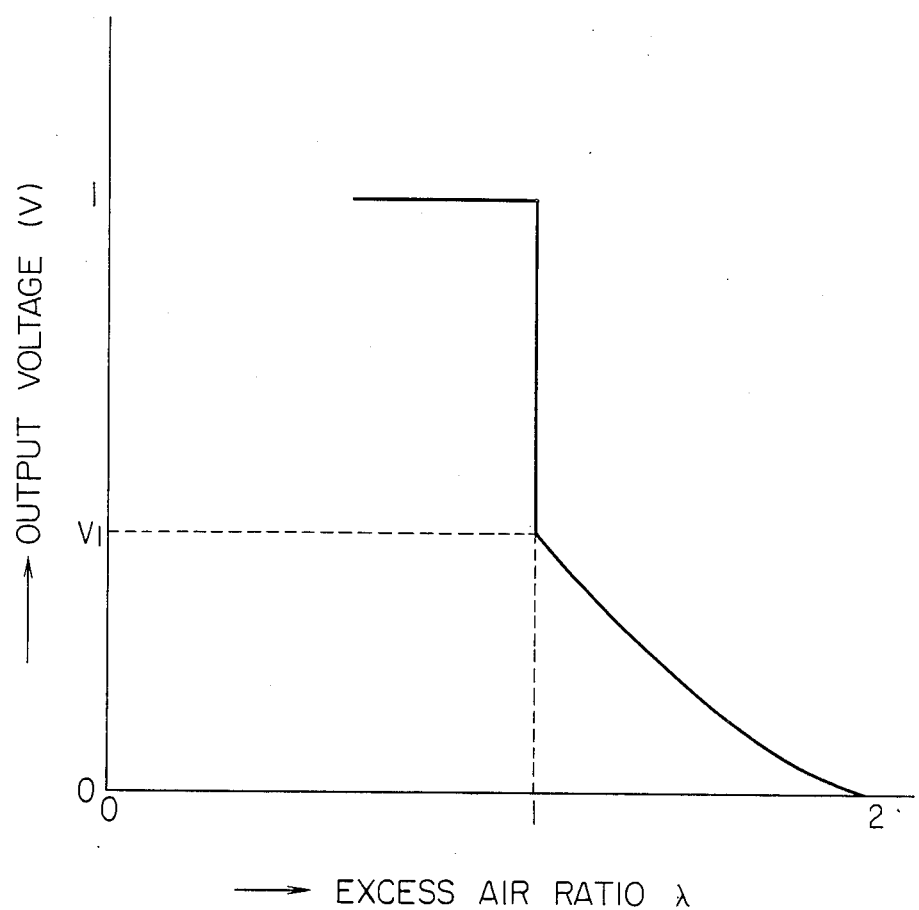
FIG. 19 is a graph of output signal adding section output characteristics implemented by the present invention, showing the relationship between the excess air ratio $\lambda$ and the output voltage.

The present inventors thus purpose an integral circuit for adding the output signals from both the sensor portions. The output characteristics of the integral circuit are shown in FIG. 19. As is apparent from FIG. 19, an output of 1 V is obtained in the rich region and is abruptly decreased to V1 at $\lambda = 1$. The output is continuously kept low in the lean region, and is set to be zero at $\lambda = 2$. The output signal adding circuit 63 in FIG. 10 is implemented to achieve the above characteristics.

Figure 20:
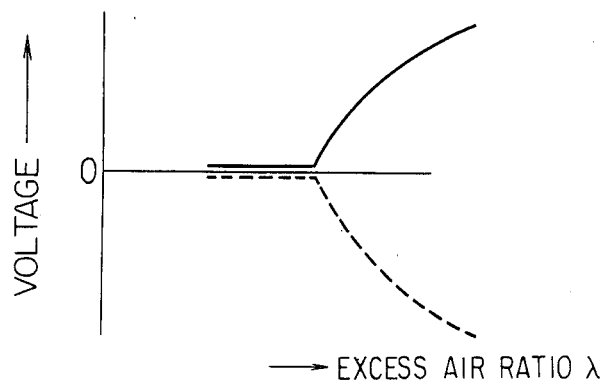
FIGS. 20 to 22 are graphs showing input to an inverting adder of FIG. 10.

The output signal adding section 63 will be described in detail. The current detector 55 converts an input current to a corresponding voltage. The voltage from the detector 55 is multiplied by a potentiometer P1 with a proportional coefficient, thereby obtaining a voltage characteristic indicated by the solid line of FIG. 20. When only the resultant signal passes through the inverting adder, an output indicated by the broken line of FIG. 20, can be obtained.

Figure 21:
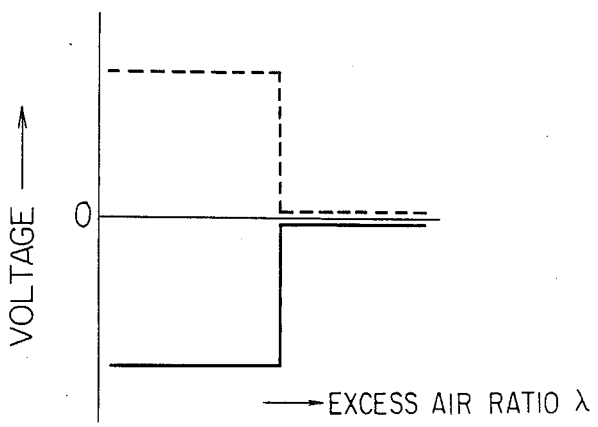

The output from the comparator 58 is shaped by the wave shaper 68. An output from the wave shaper 68 is a negative constant voltage in the rich region and is zero in the lean region. When the output from the wave shaper 68 is multiplied by a potentiometer P2 with a proportional coefficient, the output is indicated by the solid line in FIG. 21. If only the multiplied signal passes through the inverting adder 69, an output is obtained, as indicated by the broken line in FIG. 21.

Figure 22:
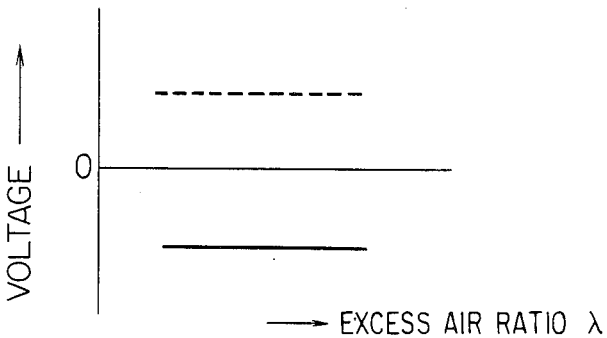

Subsequently, the negative constant voltage is supplied to a potentiometer P3 to obtain a signal indicated by the solid line in FIG. 22. If only this signal passes through the inverting adder, a signal indicated by the broken line in FIG. 22. can be obtained.

In practice, the three outputs from the potentiometers P1, P2 and P3 are simultaneously added by the inverting adder 69. A signal obtained by three signals indicated by the broken lines appears as the output from the inverting adder 69. A sum signal is shown in FIG. 19.

A limiting electric current type oxygen sensor for generating an output current in response to the oxygen gas concentration, a resistive type oxygen sensor, the resistance of which is greatly changed in response to a change in oxygen partial pressure, and a heater are integrally formed on a porous substrate in accordance with a thin film techniques. An air-fuel ratio falling within a wide range from the theoretical air-fuel ratio to the lean region can be detected. The air-fuel ratio sensor according to the present invention has bood stability, good reproducibility, high response, a compact structure and low power consumption.

What is claimed is:

1. An air-fuel ratio sensor comprising:
    a porous substrate having a porosity of 2% to 40% and a pore diameter of 0.02 μm to 1.2 μm;
    a limiting electric current type oxygen sensor portion having a first electrode, a solid electrolytic thin film and a second electrode which are sequentially formed on said porous substrate, said first electrode being gas permeable, said solid electrolytic thin film having a specific crystal orientation, a thickness of 0.1 μm to 30 μm and crystallinity;
    a resistive type oxygen sensor portion having an oxide semiconductor thin film and interdigital electrodes which are formed on said porous substrate, said oxide semiconductor thin film having a resistance which changes in response to oxygen partial pressure, said interdigital electrodes being formed on one or both surfaces of said oxide semiconductor thin film; and
    a heater formed on at least one surface of said porous substrate.

2. A sensor according to claim 1, wherein a ratio x/t of a distance x between an end of said electrolytic thin film and an end of said first electrode to a thickness t of said porous substrate is not less than 0.75.

3. An air-fuel ratio detecting apparatus comprising an air-fuel ratio sensor having: a porous substrate having a porosity of 2% to 40% and a pore diameter of 0.02 μm to 1.2 μm; a limiting electric current type oxygen sensor portion having a first electrode, a solid electrolytic thin film and a second electrode which are sequentially formed on said porous substrate, said first electrode being gas permeable, said solid electrolytic thin film having a specific crystal orientation, a thickness of 0.1 μm to 30 μm and crystallinity; a resistive type oxygen sensor portion having an oxide semiconductor thin film and interdigital electrodes which are formed on said porous substrate, said oxide semiconductor thin film being changeable in resistance in response to oxygen partial pressure, said interdigital electrodes being formed on one or both surfaces of said oxide semiconductor thin film; a heater formed on at least one surface of said porous substrate; and a porous ceramic coating layer for covering the overall structure, said porous cermic coating layer being adapted to carry a catalyst, a ratio x/t of a distance x between an end of said electrolytic thin film and an end of said first electrode to a thickness t of said porous substrate being not less than 0.75, a limiting electric current measuring voltage source for generating a voltage applied to said limiting electric current type oxygen sensor portion, a current detector for detecting a current flowing through said limiting electric current type oxygen sensor portion upon an application of the voltage thereto, a resistance detector for detecting the resistance of said resistive type oxygen sensor portion, a comparator/discriminator for comparing an output from said resistance detector with a reference value and discriminating a fuel rich or fuel lean state, a switching controller for controlling switching connection between said limiting electric current measuring voltage source and said limiting electric current type oxygen sensor portion such that said limiting electric current measuring voltage source is connected to said limiting electric current type oxygen sensor portion when a predetermined period of time has elapsed after the fuel rich state changes to the fuel lean state, and that said limiting electric current measuring voltage source is disconnected from said limiting electric current type oxygen sensor portion when the fuel lean state changes to the fuel rich state, and an output signal adding section for adding an output signal from said limiting electric current type oxygen sensor portion and an output signal from said resistive type oxygen sensor portion and generating an output signal representing an air-fuel ratio.

4. An apparatus according to claim 3, wherein said comparator/discriminator discriminates a switching timing from the fuel lean state to the fuel rich state by increasing the reference value.

5. An apparatus according to claim 3, wherein said switching controller comprises a relay circuit for connecting/disconnecting said limiting electric current measuring voltage source to/from said limiting electric current type sensor portion, and a lean delay time circuit for delaying an output signal from said cmparator/discriminator by a predetermined delay time and supplying a delayed signal as a control signal to said relay circuit.

6. An apparatus according to claim 3, wherein said output signal adding section has an inverting adder, the input terminals of which are respectively connected to level regulators, said inverter adder being adapted to add the output signal from said current detector, the output signal from said comparator/discriminator and a negative DC bias signal.

7. An apparatus according to claim 6, further comprising a wave shaper for waveshaping the output signal from said comparator/discriminator and supplying a waveshaped output to said inverting adder.

* * * * *